United States Patent [19]
Limrell et al.

[11] Patent Number: 6,152,897
[45] Date of Patent: Nov. 28, 2000

[54] SYRINGE

[75] Inventors: Karin Limrell, Sollentuna; Ebba Florin-Robertsson, Stockholm; Elvy Hökby, Enskede; Ulf Nilsson, Ekerö; Anders Ström, Enskede, all of Sweden

[73] Assignee: Pharmacia & Upjohn AB, Stockholm, Sweden

[21] Appl. No.: 09/196,514

[22] Filed: Nov. 20, 1998

[30] Foreign Application Priority Data

Nov. 28, 1997 [SE] Sweden .................................. 9704405

[51] Int. Cl.$^7$ .................................................. A61M 37/00
[52] U.S. Cl. .............................................. 604/82; 604/191
[58] Field of Search ................................ 604/82, 84–92, 604/191

[56] References Cited

U.S. PATENT DOCUMENTS

| | | |
|---|---|---|
| 4,968,299 | 11/1990 | Ahlstrand et al. . |
| 5,158,546 | 10/1992 | Haber et al. . |
| 5,171,219 | 12/1992 | Fujioka et al. . |
| 5,281,198 | 1/1994 | Haber et al. . |
| 5,454,786 | 10/1995 | Harris . |

FOREIGN PATENT DOCUMENTS

| | | |
|---|---|---|
| 0409870 | 10/1994 | European Pat. Off. . |
| WO9809614 | 10/1989 | WIPO . |
| WO9118621 | 12/1991 | WIPO . |
| WO9401150 | 1/1994 | WIPO . |
| WO9403198 | 2/1994 | WIPO . |

*Primary Examiner*—Mark Bockelman
*Attorney, Agent, or Firm*—Dinsmore & Shohl LLP

[57] ABSTRACT

The invention relates to a one-dose syringe comprising a first chamber with a freeze-dried composition comprising a protein in an amount of less than 1.4 mg, amino acid and stabilizer where the weight ratio between protein and amino acid versus stabilizer is less than 1.5 and in which the ratio of the weight of the dry component versus the cake volume in the first chamber is above 12 mg/ml, and a second chamber with an aqueous reconstitution solution with an injectable volume of less than 0.5 ml.

11 Claims, No Drawings

SYRINGE

FIELD OF THE INVENTION

The present invention relates to a one-dose syringe comprising a first chamber with a freeze-dried composition comprising a protein in an amount of less than 1.4 mg, amino acid and stabilizer where the weight ratio between protein and amino acid versus stabilizer is less than 1.5 and in which the ratio of the weight of the dry component versus the cake volume in the first chamber is above 12 mg/ml, and a second chamber with an aqueous reconstitution solution with an injectable volume of less than 0.5 ml.

BACKGROUND OF THE INVENTION

Proteins, which often are sensitive to storage in liquids, are normally freeze-dried and reconstituted by the patient shortly before injection.

When preparing a syringe with a therapeutical amount of a protein for the patient, important criteria are:

Acceptable stability of the powder before reconstitution. The preparation should have at least as good quality as freeze-dried products on the market. The dried product should be able to be stored at room temperature, at least for a certain time.

No pain when given to patients, e.g. by using an isotonic solution and a small injection volume.

Acceptable reconstitution time.

A device for preparation of an injectable solution of substances sensitive to degradation is described in U.S. Pat. No. 4,968,299, and which is available under the trademark KabiPen® on the market. With KabiPen® the patient is provided with a device which is rather simple to handle. The device comprises a two-chamber ampoule Genomix® containing hGH (human Growth Hormone) as a lyophilized powder in one of the compartments and a reconstitution solution in the other. The patient reconstitutes the product before use. The reconstituted product is then stable for 3 weeks when stored at 2–8° C. This device is a multiple-dose syringe.

There is also a one dose device on the market for growth hormone available under the trademark KabiQuick®, which has an injection volume of 0.5 ml or more.

In the patent application WO 89/09614, of Genentech, a stabilized formulation of hGH comprising glycine, mannitol and a buffer is disclosed and in a preferred embodiment a non-ionic surfactant such as polysorbate 80 is added. Sodium-phosphate is suggested as buffer substance. The formulation has an increased stability in a lyophilized formulation and upon reconstitution. The final ratio of the ingredients is obtained by buffer exchange on a gel filtration column.

Nothing is mentioned about the volume injected to the patient, nor the amount of the protein.

In the patent application WO 91/18621 (GENENTECH) mannitol is generally mentioned as carrier for stability of GH and IGF.

The patent application WO 94/03198 (GENENTECH) discloses an aqueous formulation with GH+ buffer+ surfactant+ mannitol.

There has been a desire to find a one dose syringe, which has an injectable volume of less than 0.5 ml and a low amount of protein per dose and which can be produced by freeze-drying without production problems.

It was noticed that when a one-dose syringe with protein in a low amount in a small injection volume was produced, problems arise when the solution in the first chamber of the syringe is freeze-dried.

The matrix of the freeze-dried cake was non-coherent, and this resulted surprisingly in blow out. The cake burst in the chamber and the protein was thus lost. This is not acceptable, not only for production reason, but also for economical reasons when a medicament including an expensive protein is produced. A solution to this problem must therefore be found.

This problem does not occur when KabiQuick or other freeze-dried protein products are prepared. It was noticed that these products have a high amount of protein and amino acid. The problem arising for a low amount of protein per dose has now been solved by the present invention.

SUMMARY OF THE INVENTION

We have now found that one possible way to produce the desired one dose syringe with a low amount of protein and a small injectable volume, is to combine the amount of growth hormone, the dry content and ratio of content of the protein and the additional components.

The present invention relates thus to a one-dose syringe comprising a first chamber with a freeze-dried composition comprising a protein in an amount of less than 1.4 mg, amino acid and stabilizer where the weight ratio between protein and amino acid versus stabilizer is less than 1.5 and in which the ratio of the weight of the dry component versus the cake volume in the first chamber is above 12 mg/ml and a second chamber with an aqueous reconstitution solution with an injectable volume of less than 0.5 ml.

This detailed description new device with the new composition can be produced without complications and stored with good stability.

The weight ratio between protein and amino acid versus stabilizer is preferably equal to or less than 1.3. The aqueous reconstitution solution has preferably an injectable volume of less than 0.3 ml. The solution may contain a preservative and or a buffer.

By stabilizer is meant a bulking agent matrix builder and/or cake former, e.g. mannitol, but not an amino acid, and the amino acid is preferably glycine, used but other amino acids such as alanine can also be used.

By isotonic agent is meant a substance for achieving the right osmolality of the injection solution.

The protein is preferably growth hormone, recombinant or nature, which can be both human and animal such as human growth hormone (hGH), bovine growth hormone (bGH) and porcine growth hormone (pGH).

HGH, is a protein consisting of a single chain of 191 amino acids. The molecule is cross-linked by two disulphide bridges and the monomeric form has a molecular weight of 22 kDa.

Two types of therapeutically useful recombinant hGH preparations are present on the market: the authentic one, e.g. Genotropin®, Pharmacia & Upjohn AB, and an analogue with an additional methionine residue at the N-terminal end, e.g. Somatonorm®).

hGH is used to stimulate linear growth in patients with hypo pituitary dwarfism or Turner's syndrome but other indications have also been suggested.

EXAMPLES

The invention is described in the following example with different formulations A–K in which different compositions and volumes were freeze-dried, see tables below. In the examples below a recombinant produced hGH has been used (GH). The solution of hGH for filling is obtained from the final gel filtration step of the bulk solution purification process. Buffer is added for adjustement of the final excipient concentration and thereafter the solution is diluted with buffer to the correct protein concentration.

By cake volume is meant dispensed volume before freeze-drying. The solvent used is water.

Examples F, I and K are according to the invention.

| Formulation | A | B |
|---|---|---|
| First chamber, mg/cylinder | | |
| GH | 0.35 | 0.34 |
| Glycine | 0.19 | 0.23 |
| Mannitol | 0.95 | 1.14 |
| Sodium phosphate | 0.02 | 0.05 |
| Disodium phosphate | 0.01 | 0.03 |
| Cake volume, ml | 0.25 | 0.3 |
| Weight of dry substances, mg | 1.5 | 1.8 |
| Ratio weight/cake volume Weigh ratio | 6.1 | 6.0 |
| GH + Glycine | 0.539 | 0.570 |
| Mannitol | 0.950 | 1.140 |
| (GH + Glycine):Mannitol | 0.567 | 0.5 |
| Cake observation | Blow out | Blow out |

The formulations A and B resulted in blow out.

In order to avoid the blow out problem the weight/cake volume ratio was raised by addition of mannitol, see table below.

| Formulation | C | D | E |
|---|---|---|---|
| First chamber, mg/cylinder | | | |
| GH | 0.33 | 0.31 | 0.33 |
| Glycine | 0.23 | 0.23 | 0.23 |
| Mannitol | 1.37 | 2.67 | 1.14 |
| Sodium phosphate | 0.05 | 0.05 | 0.05 |
| Disodium phosphate | 0.03 | 0.03 | 0.03 |
| Cake volume, ml | 0.3 | 0.3 | 0.3 |
| Weight of dry substances, mg | 2.0 | 3.3 | 1.8 |
| Ratio weight/cake volume Weight ratio | 6.7 | 11.0 | 5.9 |
| GH + Glycine | 0.560 | 0.541 | 0.560 |
| Mannitol | 1.374 | 2.670 | 1.140 |
| (GH + Glycine):Mannitol | 0.407 | 0.202 | 0.491 |
| Cake observation | Blow out | Blow out | Blow out |

However, the problem with blow out remained. The formulations C, D and E resulted all in blow out.

Instead the cake volume was lowered in order to increase the weight/cake volume ratio.

| Formulation | F | G | H |
|---|---|---|---|
| First chamber, mg/cylinder | | | |
| GH | 0.32 | 0.33 | 0.32 |
| Glycine | 0.33 | 0.23 | 0.23 |
| Mannitol | 1.65 | 1.14 | 1.14 |
| Sodium phosphate | 0.05 | 0.05 | 0.05 |
| Disodium phosphate | 0.03 | 0.03 | 0.03 |
| Cake volume, ml | 0.1 | 0.15 | 0.2 |
| Weight of dry substances, mg | 2.4 | 1.8 | 1.8 |
| Ratio weight/cake volume Weight ratio | 23.8 | 11.8 | 8.9 |
| GH + Glycine | 0.651 | 0.560 | 0.555 |
| Mannitol | 1.650 | 1.140 | 1.140 |
| (GH + Glycine):Mannitol | 0.394 | 0.49 | 0.486 |
| Cake observation | Good | Blow out | Blow out |

The result was, that the lower the volume the better the cake appearance. The conclusion was that for small growth hormone amounts the weight/cake volume ratio has to be raised by lowering the filling volume. Raising by increasing the mannitol amount is not successful.

These results were confirmed in two more experiments, see table below.

| Formulation | I | K |
|---|---|---|
| First chamber, mg/cylinder | | |
| GH | 0.35 | 1.06 |
| Glycine | 0.23 | 0.23 |
| Mannitol | 1.14 | 1.14 |
| Sodium phosphate | 0.05 | 0.05 |
| Disodium phosphate | 0.03 | 0.03 |
| Cake volume, ml | 0.1 | 0.15 |
| Weight of dry substances, mg | 1.8 | 2.5 |
| Ratio weight/cake volume Weight ratio | 18.0 | 16.7 |
| GH + Glycine | 0.586 | 1.288 |
| Mannitol | 0.140 | 1.140 |
| (GH + Glycine):Mannitol | 0.567 | 1.129 |
| Cake observation | Good | Good |

Conclusion:

The observation that the cake volume should be lowered in order to increase the weight/cake volume ratio was confirmed. The lower the volume, the better the cake appearance. For small growth hormone amounts the weight/cake volume ratio thus has to be raised by lowering the filling volume. Raising by increasing the mannitol amount is not successful.

This is valid for formulations where the weight ratio between protein and amino acid versus stabilizer is less than 1.5.

What is claimed is:

1. One-dose syringe, comprising:
   i) a first chamber containing a freeze-dried composition comprising growth hormone in an amount of less than 1.4 mg, mannitol and amino acid wherein the weight ratio between protein and amino acid versus stabilizer is less than 1.5 and the ratio of the weight of the freeze dried component versus the cake volume is above 12 mg/ml; and ii) a second chamber containing an aqueous reconstitution solution with an injectable volume of less than 0.5 ml.

2. Syringe according to claim 1 in which the ratio of the weight of the freeze dried component versus the cake volume in the first chamber is above 15 mg/ml.

3. Syringe according to claim 1, wherein the amino acid is glycine.

4. Syringe according to claim 1, wherein the amino acid is alanine.

5. Syringe according to claim 1, wherein the first chamber comprises a buffer.

6. Syringe according to claim 5, wherein the buffer comprises sodium phosphate.

7. Syringe according to claim 1, wherein the second chamber comprises isotonic agent.

8. Syringe according to claim 1, wherein the growth hormone is human growth hormone.

9. Syringe according to claim 8, wherein the amino acid is glycine.

10. Syringe according to claim 8, wherein the second chamber comprises isotonic agent.

11. Syringe according to claim 1, wherein the amino acid is glycine or alanine.

* * * * *